(12) United States Patent
Cho et al.

(10) Patent No.: US 11,351,260 B2
(45) Date of Patent: Jun. 7, 2022

(54) PHOTOCLEAVABLE COBALT-NITROSYL COMPLEX AND NITRIC OXIDE CARRIER CONTAINING THE SAME

(71) Applicant: DAEGU GYEONGBUK INSTITUTE OF SCIENCE AND TECHNOLOGY, Daegu (KR)

(72) Inventors: Jaeheung Cho, Daegu (KR); Daeha Seo, Daegu (KR); Jisu Choe, Daegu (KR)

(73) Assignee: DAEGU GYEONGBUK INSTITUTE OF SCIENCE AND TECHNOLOGY, Daegu (KR)

( * ) Notice: Subject to any disclaimer, the term of this patent is extended or adjusted under 35 U.S.C. 154(b) by 21 days.

(21) Appl. No.: 16/869,896

(22) Filed: May 8, 2020

(65) Prior Publication Data
US 2021/0052730 A1    Feb. 25, 2021

(30) Foreign Application Priority Data
Aug. 22, 2019  (KR) .................. 10-2019-0103327

(51) Int. Cl.
*A61K 41/00* (2020.01)
*A61K 33/00* (2006.01)
*C07F 15/06* (2006.01)

(52) U.S. Cl.
CPC .......... *A61K 41/0057* (2013.01); *A61K 33/00* (2013.01); *C07F 15/065* (2013.01)

(58) Field of Classification Search
CPC .... A61K 41/0057; A61K 33/00; C07F 15/065
See application file for complete search history.

(56) References Cited

U.S. PATENT DOCUMENTS 5,936,082 A  *  8/1999  Bauer ..................... A61P 43/00
                                               540/145

OTHER PUBLICATIONS

Shin, S. et al. "Artificial Control of Cell Signaling Using a Photocleavable Cobalt-(III)—Nitrosyl Complex" Angew. Chem. Int. Ed. 2019, 58, 10126-10131; published May 20, 2019 (Year: 2019).*
Khusnutdinova, J.R. et al. "Late First-Row Transition Metal Complexes of a Tetradentate Pyridinophane Ligand: Electronic Properties and Reactivity Implications" Inorg. Chem. 2013, 52, 3920-3932 (Year: 2013).*
Kuz'min, V.E. et al. "Investigation of anticancer activity of macrocyclic Schiff bases by means of 4D-QSAR based on simplex representation of molecular structure" SAR and QSAR in Environmental Research, vol. 16, No. 3, Jun. 2005, 219-230 (Year: 2005).*
Richter-Addo, G.B. et al. "Synthesis, Characterization, and Spectroelectrochemistry of Cobalt Porphyrins Containing Axially Bound Nitric Oxide" Inorg. Chem. 1996, 35, 6530-6538 (Year: 1996).*
Wessel, A.J. et al. "Improved synthesis of symmetrically & asymmetrically N-substituted pyridinophane derivatives" Org. Biomol. Chem., 2017, 15, 9923-9931 (Year: 2017).*
Khusnutdinova, J.R. et al. "Late First-Row Transition Metal Complexes of a Tetradentate Pyridinophane Ligand: Electronic Properties and Reactivity Implications." *Inorganic Chemistry* 52 (2013): 3920-3932.
Korean Office Action dated Jan. 26, 2021 issued in corresponding Korean Appln. No. 10-2019-0103327.
Korean Decision to Grant dated Apr. 9, 2021 issued in corresponding Korean Appln. No. 10-2019-0103327.
Grossi et al., Sodium Nitroprusside: Mechanism of NO Release Mediated by Sulfhydryl-Containing Molecules, Journal of Medicinal Chemistry, American Chemical Society, 2005, 48, 2622-2626, Italy.

* cited by examiner

*Primary Examiner* — Andrew S Rosenthal
(74) *Attorney, Agent, or Firm* — Harness, Dickey & Pierce, P.L.C.

(57) ABSTRACT

The present invention relates to a cobalt-nitrosyl complex having photocleavable ligands. The cobalt-nitrosyl complex provided in one aspect of the present invention is adept in the delivery of NO, with exquisite temporal control using light, without gene editing. In addition, the complex provided in one aspect of the present invention is excellent in biocompatibility because it is chemically stable, non-toxic at cell level, and non-perturbative in cellular environments.

8 Claims, 9 Drawing Sheets
(6 of 9 Drawing Sheet(s) Filed in Color)
Specification includes a Sequence Listing.

30 min after example 1 complex treatment with 1min irradiation

PHOTOCLEAVABLE COBALT-NITROSYL COMPLEX AND NITRIC OXIDE CARRIER CONTAINING THE SAME

REFERENCE TO A SEQUENCE LISTING SUBMITTED VIA EFS-WEB

The content of the ASCII text file of the sequence listing named "18931-23 2020-05-07 Sequence-Listing ST25," which is 1.85 kb in size, was created on May 7, 2020 and electronically submitted via EFS-Web herewith is incorporated herein by reference in its entirety.

CROSS-REFERENCES TO RELATED APPLICATION

This patent application claims the benefit of and priority to Korean Patent Application No. 10-2019-0103327, filed on Aug. 22, 2019, under 35 U.S.C. § 119, the contents of which are incorporated herein by reference.

BACKGROUND OF THE INVENTION

1. Field of the Invention

The present invention relates to a photocleavable cobalt-nitrosyl complex and a nitric oxide carrier comprising the same.

2. Description of the Related Art

Cells use gaseous signaling molecules as much as proteins to transmit biochemical information efficiently, as they possess higher productive efficiency, membrane permeability, and biochemical reactivity than the proteins. Gasotransmitters are enzymatically synthesized and are quantitatively regulated for various specific physiological functions. Endogenously synthesized nitric oxide (NO), obtained through nitric oxide synthase (NOS), for example, has a higher diffusivity ($D_{NO}$=2.2-4.5×$10^3$ μm² s$^{-1}$ in $H_2O$) and shorter life-time (approximately 1 s) than proteins. The signaling pathway triggered by NO is directly linked to the endocrine and paracrine cell-to-cell communications.

Despite their high chemical reactivity and anomalousness of diffusion, gasotransmitters have target specificity, and they can be generated in a well-regulated fashion. However, it remains unclear how cells precisely control the gaseous molecules to determine their specific cellular behaviors. To address this issue, biochemical studies of the NO pathway have been performed using conventional NO donors, such as sodium nitroprusside and S-nitroso-N-acetyl-DL-penicillamine. However, because of their limitations in the intrinsic chemical perturbations of amino acids (reaction with cysteine or glutathione), and the time they take to release, the development of novel chemicals with faster responses to a stimulus would be invaluable.

The present inventors prepared cobalt(III)-nitrosyl complex, a synthetic inorganic complex with bioregulatory photocleavable ligands. The complex according to the present invention is chemically stable, biocompatible, and exhibits non-perturbative properties in cellular environments. The complex according to the present invention is also adept in the delivery of NO, with exquisite temporal control using light, without gene editing.

SUMMARY OF THE INVENTION

In an aspect of the present invention, it is an object of the present invention to provide a photocleavable cobalt-nitrosyl complex, an inorganic complex having photocleavable ligands.

In another aspect of the present invention, it is an object of the present invention to provide a method for preparing the photocleavable cobalt-nitrosyl complex.

In another aspect of the present invention, it is also an object of the present invention to provide a nitric oxide carrier comprising the photocleavable cobalt-nitrosyl complex.

To achieve the above objects, in an aspect of the present invention, the present invention provides a cobalt-nitrosyl complex represented by formula 1 below.

[Formula 1]

(In formula 1, sol is a compound selected from the group consisting of $H_2O$, ether solvents such as $CH_3CN$, tetrahydrofuran, dioxane, dichloromethane and 1,2-dimethoxyethane, aromatic hydrocarbon solvents such as benzene, toluene and xylene, dimethyl formamide (DMF), and dimethyl sulfoxide (DMSO);

L is $R^1$ and $R^2$ are independently hydrogen, nonsubstituted or substituted straight or branched $C_{1-10}$ alkyl, $C_{3-10}$ cycloalkyl, $C_{6-10}$ aryl, or $C_{6-10}$ aryl $C_{1-3}$ alkyl, wherein the substituted straight or branched $C_{1-10}$ alkyl, $C_{3-10}$ cycloalkyl, $C_{6-10}$ aryl, or $C_{6-10}$ aryl $C_{1-3}$ alkyl is independently $C_{1-10}$ alkyl, $C_{3-10}$ cycloalkyl, $C_{6-10}$ aryl, or $C_{6-10}$ aryl $C_{1-3}$ alkyl substituted with one or more substituents selected from the group consisting of halogen, hydroxy, nitro, nitryl, $C_{1-3}$ alkyl and $C_{1-3}$ alkoxy;

X and Y are independently hydrogen, halogen, nonsubstituted or substituted straight or branched $C_{1-8}$ alkyl, $C_{3-8}$ cycloalkyl, $C_{6-8}$ aryl, or $C_{6-8}$ aryl $C_{1-3}$ alkyl, wherein the substituted straight or branched $C_{1-8}$ alkyl, $C_{3-8}$ cycloalkyl, $C_{6-8}$ aryl, or $C_{6-8}$ aryl $C_{1-3}$ alkyl is independently $C_{1-3}$ alkyl, $C_{3-8}$ cycloalkyl, $C_{6-8}$ aryl, or $C_{6-8}$ aryl $C_{1-3}$ alkyl substituted with one or more substituents selected from the group consisting of halogen, hydroxy, nitro, nitryl, $C_{1-3}$ alkyl and $C_{1-3}$ alkoxy; and m and n are independently integers of 0 to 3).

In another aspect of the present invention, the present invention provides a preparation method of a cobalt-nitrosyl complex represented by formula 1 comprising the step of preparing a compound represented by formula 1 by reacting a compound represented by formula 2 with nitric oxide (NO), as shown in reaction formula 1 below:

[Reaction Formula 1]

(In reaction formula 1,

L and sol are as defined in formula 1 above).

In another aspect of the present invention, the present invention also provides a nitric oxide carrier comprising the photocleavable cobalt-nitrosyl complex represented by formula 1.

Advantageous Effect

The cobalt-nitrosyl complex provided in one aspect of the present invention has photocleavable ligands, and thus, when irradiated with light, it is adept in the delivery of NO, with exquisite temporal control using light, without gene editing. In addition, the complex provided in one aspect of the present invention is excellent in biocompatibility because it is chemically stable, non-toxic at cell level and exhibits non-perturbative properties in cellular environments.

BRIEF DESCRIPTION OF THE DRAWINGS

The application filed contains at least one drawing executed in color. Copies of this patent application publication with color drawings will be provided by the Office upon request and payment of the necessary fee.

DESCRIPTION OF THE PREFERRED EMBODIMENTS

Hereinafter, the present invention is described in detail.

The embodiments of this invention can be modified in various other forms, and the scope of the present invention is not limited to the embodiments described below. It is well understood by those in the art who has the average knowledge on this field that the embodiments of the present invention are given to explain the present invention more precisely. In addition, the "inclusion" of an element throughout the specification does not exclude other elements, but may include other elements, unless specifically stated otherwise.

In one aspect of the present invention, the present invention provides a cobalt-nitrosyl complex represented by formula 1 below.

$$[Co^{III}(L)(NO)(sol)]^{2+} \quad \text{[Formula 1]}$$

(In formula 1, sol is a compound selected from the group consisting of $H_2O$, ether solvents such as $CH_3CN$, tetrahydrofuran, dioxane, dichloromethane and 1,2-dimethoxyethane, aromatic hydrocarbon solvents such as benzene, toluene and xylene, dimethyl formamide (DMF), and dimethyl sulfoxide (DMSO), but not always limited thereto;

L is $R^1$ and $R^2$ are independently hydrogen, nonsubstituted or substituted straight or branched $C_{1-10}$ alkyl, $C_{3-10}$ cycloalkyl, $C_{6-10}$ aryl, or $C_{6-10}$ aryl $C_{1-3}$ alkyl, wherein the substituted straight or branched $C_{1-10}$ alkyl, $C_{3-10}$ cycloalkyl, $C_{6-10}$ aryl, or $C_{6-10}$ aryl $C_{1-3}$ alkyl is independently $C_{1-10}$ alkyl, $C_{3-10}$ cycloalkyl, $C_{6-10}$ aryl, or $C_{6-10}$ aryl $C_{1-3}$ alkyl substituted with one or more substituents selected from the group consisting of halogen, hydroxy, nitro, nitryl, $C_{1-3}$ alkyl and $C_{1-3}$ alkoxy;

X and Y are independently hydrogen, halogen, nonsubstituted or substituted straight or branched $C_{1-8}$ alkyl, $C_{3-8}$ cycloalkyl, $C_{6-8}$ aryl, or $C_{6-8}$ aryl $C_{1-3}$ alkyl, wherein the substituted straight or branched $C_{1-8}$ alkyl, $C_{3-8}$ cycloalkyl, $C_{6-8}$ aryl, or $C_{6-8}$ aryl $C_{1-3}$ alkyl is independently $C_{1-8}$ alkyl, $C_{3-8}$ cycloalkyl, $C_{6-8}$ aryl, or $C_{6-8}$ aryl $C_{1-3}$ alkyl substituted with one or more substituents selected from the group consisting of halogen, hydroxy, nitro, nitryl, $C_{1-3}$ alkyl and $C_{1-3}$ alkoxy; and m and n are independently integers of 0 to 3).

In another aspect, $R^1$ and $R^2$ are independently nonsubstituted or substituted straight or branched $C_{1-8}$ alkyl, or $C_{3-6}$ cycloalkyl, wherein the substituted straight or branched $C_{1-8}$ alkyl, or $C_{3-6}$ cycloalkyl is independently $C_{1-8}$ alkyl, or $C_{3-6}$ cycloalkyl substituted with one or more substituents selected from the group consisting of halogen, hydroxy, nitro, nitryl, $C_{1-3}$ alkyl and $C_{1-3}$ alkoxy;

X and Y are independently hydrogen, halogen, nonsubstituted or substituted straight or branched $C_{1-5}$ alkyl, or $C_{3-6}$ cycloalkyl, wherein the substituted straight or branched $C_{1-5}$ alkyl, or $C_{3-6}$ cycloalkyl, is independently $C_{1-5}$ alkyl, or $C_{3-6}$ cycloalkyl substituted with one or more substituents selected from the group consisting of halogen, hydroxy, nitro, nitryl, $C_{1-3}$ alkyl and $C_{1-3}$ alkoxy; and m and n are independently integers of 0 to 2.

In another aspect, $R^1$ and $R^2$ are independently nonsubstituted or substituted straight or branched $C_{1-3}$ alkyl, wherein the substituted straight or branched $C_{1-3}$ alkyl is $C_{1-3}$ alkyl substituted with one or more substituents selected from the group consisting of halogen, hydroxy, $C_{1-3}$ alkyl and $C_{1-3}$ alkoxy;

X and Y are independently hydrogen, nonsubstituted or substituted straight or branched $C_{1-2}$ alkyl, wherein the substituted straight or branched $C_{1-2}$ alkyl is independently $C_{1-2}$ alkyl substituted with one or more substituents selected from the group consisting of halogen, hydroxy, $C_{1-3}$ alkyl and $C_{1-3}$ alkoxy; and m and n are independently integers of 0 or 1.

In another aspect, sol is $CH_3CN$; and

L is N,N'-dimethyl-2,11-diaza[3,3] (2,6)-pyridinophane.

In another aspect of the present invention, the present invention provides a preparation method of a cobalt-nitrosyl complex represented by formula 1 comprising the step of preparing a compound represented by formula 1 by reacting a compound represented by formula 2 with nitric oxide (NO), as shown in reaction formula 1 below:

[Reaction Formula 1]

(In reaction formula 1,

L and sol are as defined in formula 1 above).

In another aspect of the present invention, the present invention also provides a nitric oxide carrier comprising the cobalt-nitrosyl complex represented by formula 1 above.

In another aspect, nitric oxide can be released from the nitric oxide carrier when the complex is irradiated with light.

In another aspect, the nitric oxide carrier can be one that artificially regulates cell signaling.

The reaction wherein nitric oxide is released by irradiating the complex with light, for example, when the sol of Formula 1 is $CH_3CN$ and the L is N,N'-dimethyl-2,11-diaza[3,3](2,6)-pyridinophane, can proceed as follows.

Practical and presently preferred embodiments of the present invention are illustrative as shown in the following preparative examples, examples and experimental examples.

However, the preparative examples, examples and experimental examples described below are merely illustrative of some of the present invention, but the present invention is not limited thereto.

<Preparative Example 1> Preparation of [Co(MDAP) $(CH_3CN)_2]^{2+}$ Complex

Step 1: Preparation of MDAP (N,N'-dimethyl-2,11-diaza[3,3] (2,6)-pyridinophane)

MDAP (N,N'-dimethyl-2,11-diaza[3,3](2,6)-pyridinophane) ligand was prepared by reacting 2,6-bis-(chloromethyl)pyridine and 2,6-bis[(N-methylamino)methyl]-pyridine at 80° C.

Step 2: Preparation of [Co((MDAP) (CH$_3$CN)$_2$]$^{2+}$ Complex

[Co (MDAP) (CH$_3$CN)$_2$] (ClO$_4$)$_2$ (H$_2$O) was prepared by reacting Co(ClO$_4$)$_2$6H$_2$O (0.1830 g, 0.50 mmol, Sigma-Aldrich, 401404, 25 g), MDAP (0.1342 g, 0.50 mmol) prepared in step 1 above in CH$_3$CN (2.0 mL), and CHCl$_3$ (2.0 mL). The mixture was stirred for 12 h, giving an orange-red solution. Then, Et$_2$O (40 mL) was added to the resulting solution, which was filtered, washed with Et$_2$O, and dried in vacuo. As a result, red powders were obtained.

Powder yield: 0.2757 g (88%).

UV/Vis (CH$_3$CN): $\lambda_{max}$ ($\varepsilon$)=487 nm (54 M$^{-1}$ cm$^{-1}$), 900 nm (18 M$^{-1}$ cm$^{-1}$).

ESI-MS (CH$_3$CN): m/z 184.1 for [Co (MDAP) (CH$_3$CN)]$^{2+}$, m/z 204.6 for [Co(MDAP) (CH$_3$CN)$_2$]$^{2+}$, m/z 426.1 for [Co(TBDAP) (ClO$_4$)]$^+$.

Anal. Calcd for C$_{20}$H$_{28}$Cl$_2$CoN$_6$O$_9$: C, 38.35; H, 4.51; N, 13.42. Found: C, 38.17; H, 4.21; N, 13.01.

The effective magnetic moment of $\mu_{eff}$=4.4 B.M. ($^1$H NMR Evans method in CH$_3$CN at 25° C.).

<Example 1> Preparation of [Co (MDAP) (NO) (CH$_3$CN)$_2$]$^{2+}$ Complex

A dark-red solution was prepared by bubbling [Co (MDAP) (CH$_3$CN)$_2$] (ClO$_4$)$_2$(H$_2$O) (0.0304 g, 0.0485 mmol) prepared in preparative Example 1 and NO gas (excess) in CH$_3$CN (1.5 mL) at −40° C. At this time, it was confirmed that the color of the reactant was changed from orange to red to dark-red. Then, Ar saturated Et$_2$O (40 mL) was added to the resulting solution to yield dark-red powders.

Powder yield: 0.0285 g (95%).

UV/Vis (CH$_3$CN): $\lambda_{max}$ ($\varepsilon$)=330 nm (4.3×10$^3$ M$^{-1}$ cm$^{-1}$), 480 nm (4.1×10$^2$ M$^{-1}$ cm$^{-1}$).

Anal. Calcd for C$_{18}$H$_{25}$Cl$_2$CoN$_6$O$_{10}$: C, 35.14; H, 4.10; N, 13.66. Found: C, 34.92; H, 3.90; N, 13.30.

<Experimental Example 1> Physicochemical Analysis of Photocleavable Cobalt-Nitrosyl Complex The following experiment was performed for the physicochemical analysis of [Co (MDAP) (NO) (CH$_3$CN)$_2$]$^{2+}$ complex prepared in Example 1.

1-1. X-Ray Crystallography

Figure 1A:
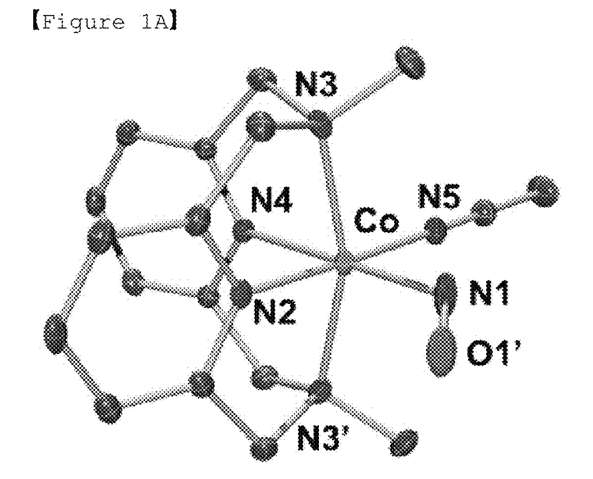
FIG. 1A is a diagram illustrating the ORTEP diagram of the complex of Example 1 according to the present invention.

Single crystals of the complex prepared in Example 1 were grown in CH$_3$CN/Et$_2$O at −40° C. As shown in FIG. 1A, the X-ray crystal structure of the complex of Example 1 exhibited mononuclear cobalt-NO complex in a distorted octahedral geometry, with four nitrogen (N) atoms of the macrocyclic MDAP ligand. At this time, one of the nitrogen atoms is derived from CH$_3$CN, and one is the nitrogen atom of NO. The N1-O1 and Co1-N1 bond lengths in the complex of Example 1 were 1.097(6) Å and 1.855(4) Å, respectively. These are comparable to those in [Co(NO) (NH$_3$)$_5$]$^{2+}$ (1.154 and 1.871 Å, respectively), [Co(NO)(en)$_2$(Cl)]$^+$ (1.109 and 1.820 Å, respectively), and [Co(NO) (en)$_2$(OClO$_3$)]$^+$ (1.15 and 1.86 Å, respectively).

1-2. UV/Vis Absorption Spectroscopy and Fourier Transform Infrared Spectrum (FT-IR)

UV/Vis spectra were recorded on a diode array spectrophotometer (Agilent, Cary 8454) equipped with a cryostat (UNISOKU Scientific Instruments, USP-203) for −40° C. or a circulating water bath (EYELA, NCB-1200) for 25° C. experiments, respectably. UV/Vis spectrum results for the complex of Example 1 were shown in FIG. 1B.

Figure 1B:
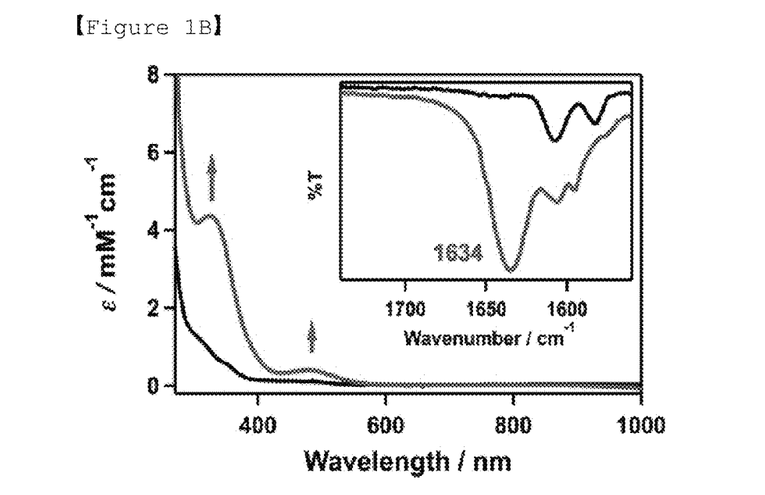
FIG. 1B is a diagram illustrating the UV/Vis absorption spectra of a complex of preparative Example 1 according to the present invention (0.25 mM, black line) and another complex of Example 1 according to the present invention (0.25 mm, red line). The inset on the right is a diagram illustrating FT-IR spectra of a complex of preparative Example 1 according to the present invention (black line) and another complex of Example 1 according to the present invention (red line).

As shown in FIG. 1B, the UV/Vis spectrum of the complex of Example 1 in CH$_3$CN contained characteristic absorption bands at $\lambda_{max}$=330 nm ($\varepsilon$=4.3×10$^3$ M$^{-1}$ cm$^{-1}$) and 480 nm (s=4.1×10$^2$ M$^{-1}$ cm$^{-1}$).

The Fourier transform infrared (FT-IR) spectrum of the complex of Example 1 displayed an NO stretching band at 1634 cm$^{-1}$ (FIG. 1B, inset), which lies within the range of previously reported values for {CoNO}$^8$ complexes (1584-1716 cm$^{-1}$).

1-3. Natural Transition Orbital (NTO) Analysis

Natural transition orbital (NTO) analysis was performed to identify the hole and particle of the lowest singlet transition. The results were shown in FIG. 2.

Figure 2:
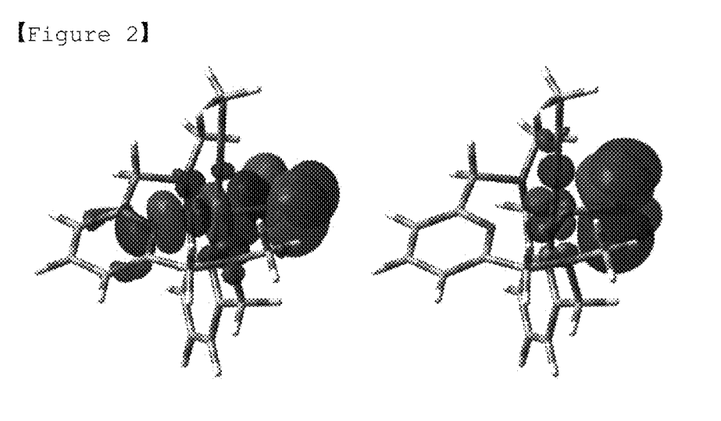
FIG. 2 is a diagram illustrating the hole (left) and particle (right) calculated from natural transition orbital (NTO) analyses of the complex of Example 1 according to the present invention.

As shown in FIG. 2, the hole involved a σ-bonding interaction between the $d_{z^2}$ orbital of Co and the π* orbital of NO. A significant anti-bonding interaction was observed in the particle dominated by the π$^{*+}$ orbital of NO, which interacted with the $d_{yz}$ orbital of Co in an out-of-phase fashion. Thus, it was confirmed that NO could be dissociated in the excited state of the complex of Example 1.

<Experimental Example 2> Evaluation of Biocompatibility of Photocleavable Cobalt-Nitrosyl Complex To confirm the chemical stability and excellent photo-induced NO-releasing property exhibited by the complex of Example 1 in aqueous conditions, the present inventors measured cell viability and cytotoxicity by analyzing varying doses of the compound of Example 1 in a culturing medium using MTT (3-(4,5-dimethylthiazol-2-yl)-2,5-diphenyltetrazolium bromide), LIVE/DEAD assay, and microscopy.

2-1. Evaluation of Cell Viability

In order to evaluate the biocompatibility of the complex of Example, the cell viability was confirmed when the complex of Example 1 was treated to cells at various concentrations. At this time, U2OS cells (purchased from the Korean Cell Line Bank, Korea) were used for the experiment.

U2OS cells cultured in DMEM (Dulbeco's modified eagle's media) containing 10% FBS, 100 unit/mL penicillin and 100 μg/mL streptomycin on T25 flask were maintained at 37° C. and in 5% CO$_2$ in a humidified incubator. U2OS cells were subcultured every 3-4 d (at 80-100% confluency).

For subculture, the cells were treated with 1.5 mL trypsin with 0.25% EDTA for 5 min, and washed with 5.0 mL DMEM with centrifugation (125 g for 5 min). The cell pellet was resuspended to 1.0 mL of DMEM by pipetting and 200 µL of cell culture fluid was subcultured to the new T25 flask containing 4.8 mL of DMEM and incubated at 37° C. and in 5% $CO_2$ in a humidified incubator.

Figure 4:
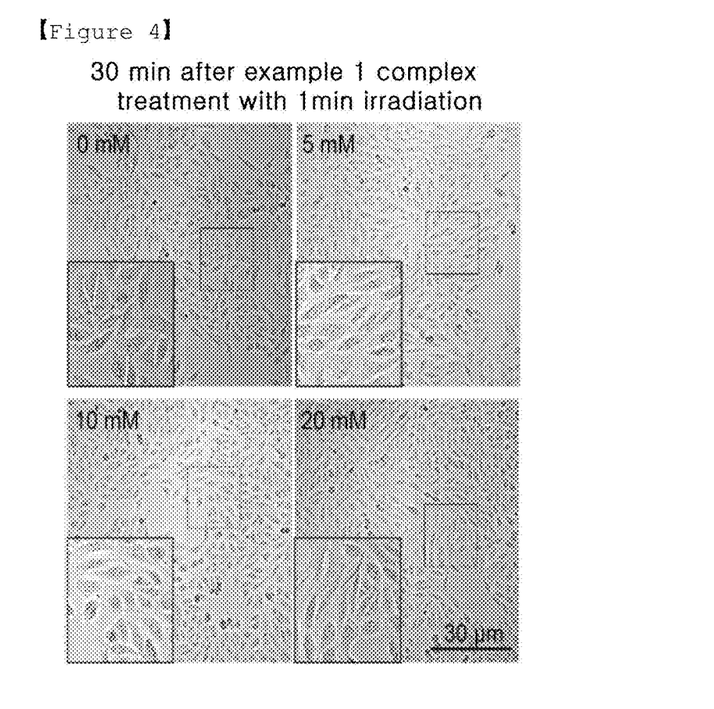
FIG. 4 is a diagram showing the bright-field images of U2OS cells under treatment of the complex of Example 1 according to the present invention (0, 5, 10, 20 mM, 30 min) and light (1 min).

Bright-field images of U2OS cells under treatment of the complex of Example 1 (0, 5, 10 and 20 mM for 30 min) and light (for 1 min) were shown in FIG. 4. As shown in FIG. 4, the cells showed no meaningful morphological changes even in higher concentration of the complex of Example 1. Therefore, it was confirmed that the complex of Example 1 was biocompatible since it did not affect cell viability.

2-2. MTT Assay

The biocompatibility of the complex of Example 1 was evaluated. Particularly, the complex of Example 1 was treated to cells and the cell proliferation was evaluated to confirm the toxicity.

MTT (3-(4,5-dimethylthiazole-2-yl)-2,5-diphenyltetrazoliumbromide) was dissolved in 1×PBS at the concentration of 5 mg/mL, which was wrapped by aluminum foil avoiding sunlight. The 8,000~10,000 cells were placed on each well in a 96-well plate, then cultured at 37° C. and in 5% $CO_2$ in a humidified incubator. Each well was washed with PBS. After washing, 200 µL of DMEM (Dulbeco's modified eagle's media) with 0.5, 1, 2.5, 5, 10, 20 mM the complex of Example 1 was added to each of the five wells and cultured for 24 h. After 1 day for the complex of Example 1 treatment, each medium was removed carefully, then the 200 µL of MTT solution diluted 10-fold with DMEM was added and washed each well and incubated for 1 h. The MTT solution was removed carefully and 100 µL of DMSO was added to each well, then the 96-well plate was shaken by a plate shaker for 30 min. After shaking, the 96-well plate absorbance at 540 nm was read by a plate reader.

Cell toxicity was determined by comparing the ratio of absorbance measured on a non-drug-loaded well. The fitting line of MTT assay was obtained by fitting Dose-response-Inhibition log (inhibitor) vs response.

Figure 5:
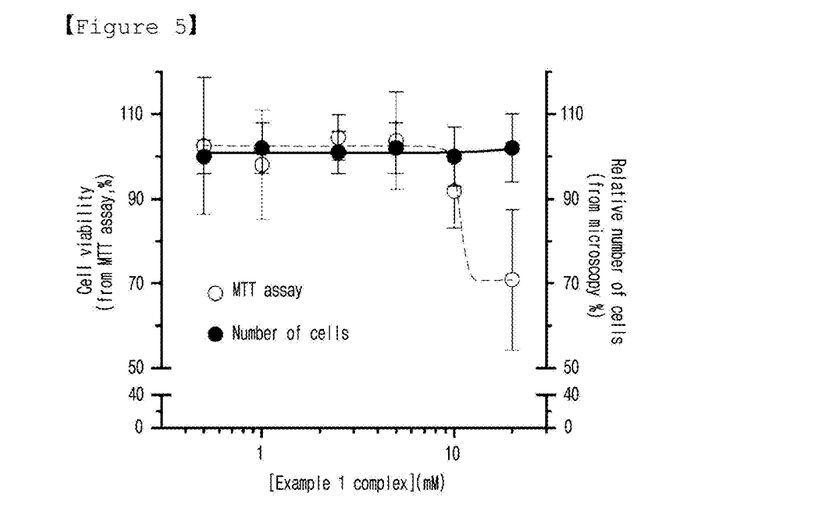
FIG. 5 is a diagram illustrating the results of MTT assay to evaluate the cell-proliferation under treatment of the complex of Example 1 according to the present invention.

FIG. 5 is a diagram illustrating the results of MTT assay (red line) to evaluate the cell-proliferation. As a result, when the complex of Example 1 was treated at the concentrations of 0.5 to 10 mM, the cell viability was not significantly different. Treatment of the complex of Example 1 with 5 mM or less showed no toxicity. Therefore, it was confirmed that the complex of Example 1 was biocompatible since it did not show toxicity when treated with the concentrations above.

2-3. LIVE/DEAD Assay

In order to evaluate the biocompatibility of the complex of Example 1, live and dead cells in the culture medium treated with the complex of Example 1 were observed under a microscope. U2OS cells were placed in a 12-well plate at 60% confluency, incubated at 37° C. and in 5% $CO_2$ for 12 hours. After washing the cells with PBS, 1 mL of DMEM (Dulbeco's modified eagle's media) containing 0.5, 1, 2.5, 5, 10 and 20 mM of the complex of Example 1 were added to the plate and incubated for additional 24 hours. For LIVE/DEAD assay, each medium was exchanged with PBS, 1 mL of solution containing 1 µM of calcein AM and 2 µM of EthD-1 was added to each well, and incubated for 30 minutes at room temperature. Then, the green fluorescence signal of live cells and the red fluorescence signal of dead cells were observed with Epi-fluorescence microscope.

Figure 6A:
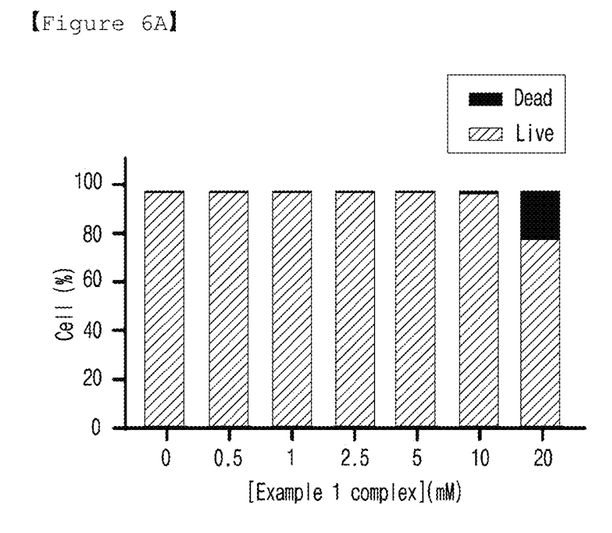
FIG. 6A is a diagram illustrating the results of LIVE/DEAD assay for cytotoxicity of the complex of Example 1 according to the present invention.
Figure 6B:
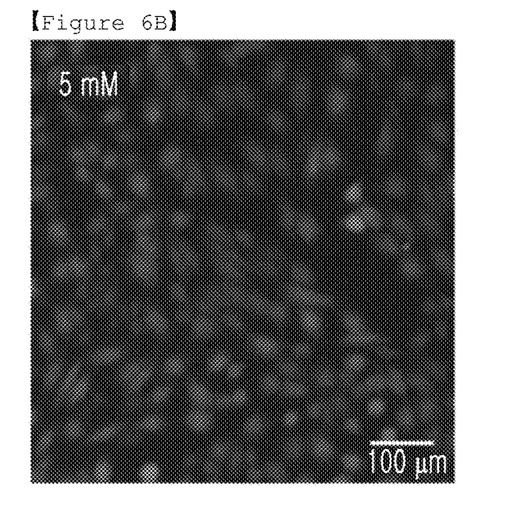
FIG. 6B is a diagram showing the live cells (green) and dead cells (red) confirmed by LIVE/DEAD assay with the treatment of 5 mM of the complex of Example 1 according to the present invention.

As a result of the LIVE/DEAD assay for cytotoxicity of the complex of Example 1, it was confirmed that the treatments of 10 mM (or less) of the complex of Example 1 was not toxic (FIG. 6A). FIG. 6B is a diagram showing the live cells (green) and dead cells (red) confirmed by LIVE/DEAD assay with the treatment of 5 mM of the complex of Example 1 observed under a microscope. Through this, it was confirmed that almost 100% cell viability could be obtained when the complex of Example 1 of 5 mM or less was treated because there was almost no toxicity.

<Experimental Example 3> Evaluation of Cell Signaling Activity of Photocleavable Cobalt-Nitrosyl Complex The following experiment was performed to evaluate the effect of NO dissociation and the artificial regulation of cell signaling when the complex of Example 1 was irradiated with light.

3-1. UV/Vis Absorption Spectroscopy

In order to confirm the NO photolysis when the complex of Example 1 was irradiated with light, the progress of the NO photolysis of the complex of Example 1 in $H_2O$ was monitored through the UV/Vis spectral change in the absorption band at 330 nm induced by irradiation with the white light. The results were shown in FIG. 3.

Figure 3:
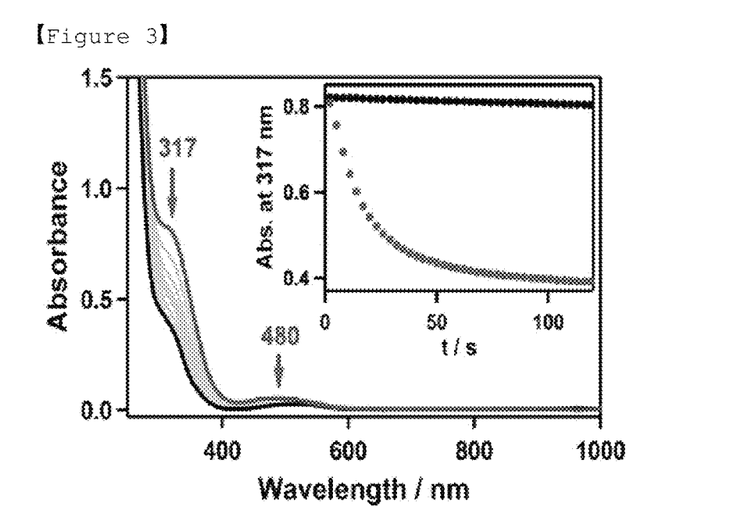
FIG. 3 is a diagram illustrating the UV/Vis absorption spectra recorded during photolysis of the complex of Example 1 according to the present invention (0.50 mM) illuminated under a xenon lamp. The inset on the right is a diagram illustrating changes in the absorbance of the complex of Example 1 according to the present invention at 317 nm with (red line) and without (black line) illumination.

As a result, in an aerobic solution of $H_2O$, the complex of Example 1 showed negligible NO release in the absence of light for 30 minutes (inset of FIG. 3, black line). However, exposure of the aqueous solution of the complex of Example 1 to white light (xenon lamp, $\lambda_{irr}$=385-740 nm, 300 W) caused rapid responses in the UV/Vis absorption spectrum (FIG. 3, red line). As shown in FIG. 3, the photo release of NO from the complex of Example 1 was rapid ($t_{1/2}$=12 s), obeying first-order kinetics. The quantum yield of the photo released NO ($\Phi_{NO}$) was determined to be 0.78 (standard ferrioxalate actionometry).

3-2. Evaluation of ERK Signal Strength

Figure 7A:
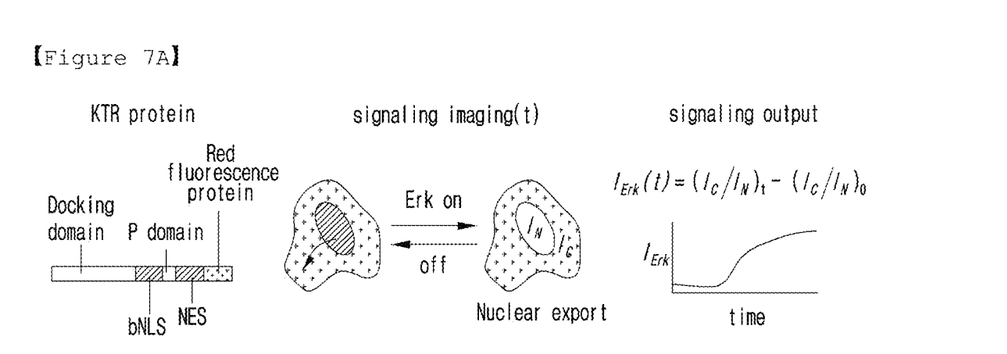
FIG. 7A is a diagram illustrating the KTR protein, the expected image from fluorescence microscopy, and the corresponding signaling output over time, from the left, respectively.

To visualize signaling activation, the present inventors developed a kinase translocation reporter (KTR) cell line that converts the process of phosphorylation into the nucleo-cytoplasmic transportation of fluorescence proteins. It is generally accepted that intracellular NO activates sGC (soluble guanylyl cyclase), and that following its downstream pathway, cGMP (cyclic guanosine monophosphate) is produced, and PKG (protein kinase G) and ERK (extracellular signal-regulated kinase) are activated. In Experimental Example 3-2, the ERK-KTR U2OS cell line was used to investigate whether cellular signaling can be governed by NO delivery, triggered by light irradiation. This cell line expresses a KTR protein, which consists of Elk1 docking domain, bNLS (bipartite nuclear localization signal), P domain, NES (nuclear export sequence), and mCherry (FIG. 7A). When the ERK is activated, it docks onto the Elk1 docking site (SEQ ID NO. 1 and SEQ ID NO. 3), before phosphorylating the bNLS and NES (SEQ ID NO. 2 and SEQ ID NO. 4) (SEQ ID NO. 1 is the protein sequence of Elk1, SEQ ID NO. 2 is the protein sequence of bNLS+NES, SEQ ID NO. 3 is the nucleotide sequence of Elk1, and SEQ ID NO. 4 is the nucleotide sequence of bNLS+NES.). The bNLS negatively regulates the concentration of the proteins at the nucleus, while the NES positively regulates nuclear export. Upon phosphorylation of the bNLS and the NES by ERK, the KTR is translocated out of the nucleus into the cytoplasm, resulting in an increase in cytoplasmic fluorescence. Therefore, the activation of ERK could be visualized through the relative intensity changes in the mCherry-derived fluorescence in the nucleus and the cytosol. In Experimental Example 3-2, the sensitivity and the heterogeneity of the ERK-KTR cell line at the single-cell level were evaluated by stimulating the ERK through the MAPK (mitogen-activated protein kinase) pathway by treating the cells with EGF (epidermal growth factor, 100 ng mL$^{-1}$).

ERK-KTR-mCherry Plasmid Generation.

To prepare the pBABE-ERK-KTR-mCherry plasmid, the cDNA of ERK-KTR-mCherry was synthesized through PCR, which was subcloned between BamHI and EcoRI enzyme sites of pBABE-puro vector that has puromycin resistance sequence. The plasmid was transformed into Top10 competent *E. coli* (Thermo Fisher, C404010), which was selected with 50 μg/mL of ampicillin, and purified with the miniprep kit (Qiagen, 27104). The concentration was measured using nanodrop. For electro-transfection, the purified plasmid was concentrated to 1 μg/μL using speedvac.

ERK Signal Activity Test Using EGF Ligand in Live Cell.

The red fluorescence signal of stable ERK-KTR cells was observed with Epi-fluorescence microscope. The cells were placed on 35 mm collagen I coated glass bottom dishes (MatTek). The cells were starved for 24 hours with 2 mL of serum-free medium to synchronize the KTR signals. The dish was placed on a pre-warmed microscope stage top incubator at 37° C. (5% $CO_2$, 80% humidity). The cells were photographed every 1 minute over 40 minutes, and 20 μL of 100 ng/μL EGF was added at 20 minutes.

Activation of ERK Signaling Using Photoactive NO Exogenous/Endogenous Delivery.

To confirm the capability of NO delivery, and NO induced cell signaling in live cells, the transfected cells were observed with a fluorescence microscope. The cells were plate on 35 mm glass bottom dishes and starved with 1.8 mL of serum-free medium for 24 hours to synchronize the ERK-KTR signals. After synchronization, the 35 mm-glass bottom dish was placed on a warmed microscope stage top incubator at 37° C. (5% $CO_2$, 80% humidity). The cells were photographed every 1 minute over 10 minutes to measure the endogenous signaling level without stimuli. For the exogenous NO delivery stimulation, 5 mM 10× complex of Example 1 was added to the cells, then the cells were irradiated with 0.38 W of white light derived from a light source 4.5 cm away for 1 minute immediately and monitored for additional 30 minutes. For the endogenous NO delivery stimulation, the cells were treated with 5 mM 10× complex of Example 1 for 10 minutes before plating on stage then washed with serum-free medium. After plating, the cells were photographed every 1 minute over 10 minutes to check if there were signaling changes through the treatment of the complex of Example 1 then, the cells were irradiated for 1 minute and monitored for additional 30 minutes.

To confirm the light effect on ERK signaling, the cells were photographed every 1 minute for 25 minutes and 5 mM 10× complex of Example 1 was added to the cells and the cells were irradiated for 1 minute at 10 minutes.

Figure 7B:
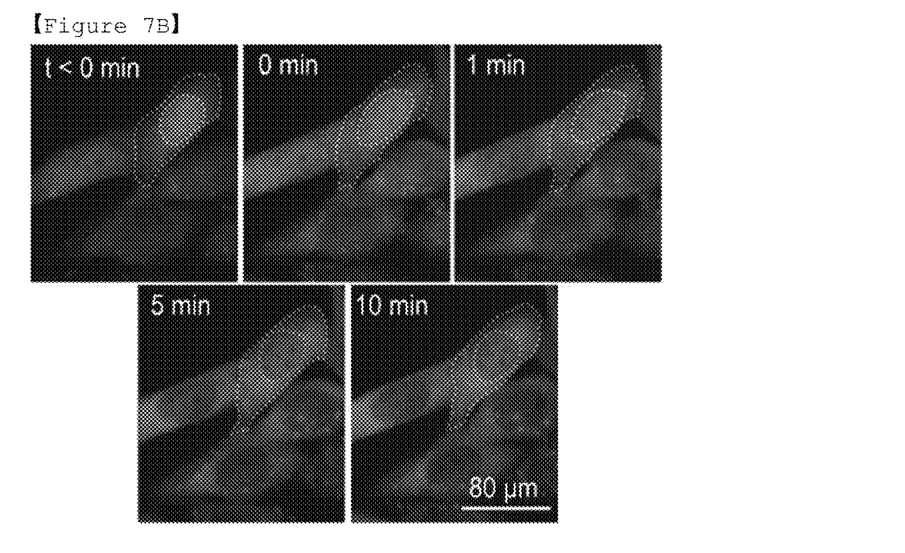
FIG. 7B is a diagram showing the representative images of ERK activation by endogenous NO molecules in ERK-KTR U2OS cells.

In Experimental Example 3-2, the present inventors applied the complex of Example 1 as an NO delivery molecule to confirm whether the NO release could be controlled in living cells. To mimic endogenous NO ($NO_{Endo}$) generation, ERK-KTR cells were cultured with 5 mM of the complex of Example 1 for 10 minutes, and the excess complex was removed by exchanging the culturing medium. Then, the cells were irradiated by hv for 1 minute (FIG. 7B). As a result, it was confirmed through the signaling intensity ($I_{ERK}(t)(I_C/I_N)_t-(I_C/I_N)_0$, FIG. 7C, green line) that the ERK-KTR proteins were translocated from the nucleus to the cytosolic region immediately after the stimulation. The resulting $I_{ERK}$ was then compared with the negative control stimulations (incubation with the complex of Example 1 without hv (FIG. 7C, orange line), hv for 1 minute without chemical treatment (FIG. 7C, purple line), and no stimuli (gray line)). As a result, it was confirmed that the NO molecules were indeed generated in the cytosol, and that they triggered ERK signaling in live cells, without any detectable phenotypic change, or the spontaneous decomposition of the complex of Example 1.

In Experimental Example 3-2, the present inventors took advantage of this ability to perform light-controlled delivery of NO to stimulate cells with exogenous conditions ($NO_{Exo}$) by treating with the complex of Example 1 and hv simultaneously (FIG. 7C, pink) to generate NO molecules before the penetration of the cell membrane by the complex of Example 1. The results showed ERK activation, which indicates that the NO molecules displayed permeability across lipid membranes. Quantitative characterization of $\Delta I_{ERK}$ for all the experiments shown in FIG. 7D revealed that the different delivery methods of NO resulted in different outcomes.

Figure 7C:
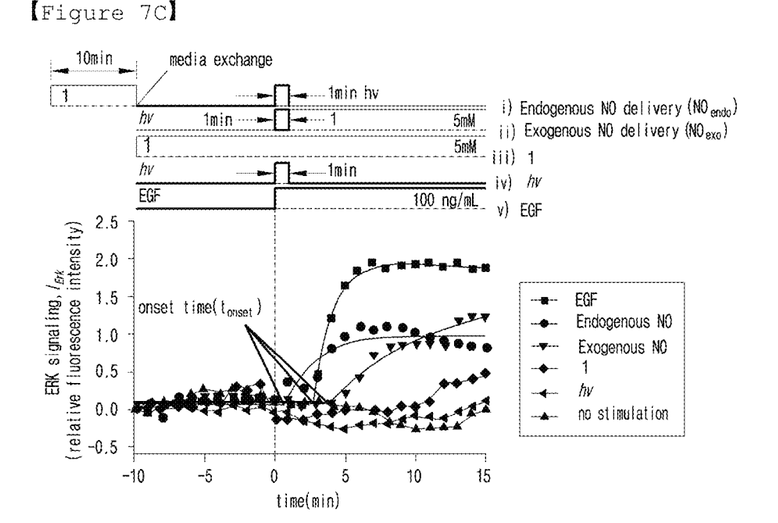
FIG. 7C is a diagram illustrating the ERK signals with relative fluorescence intensity over time in various environments.
Figure 7D:
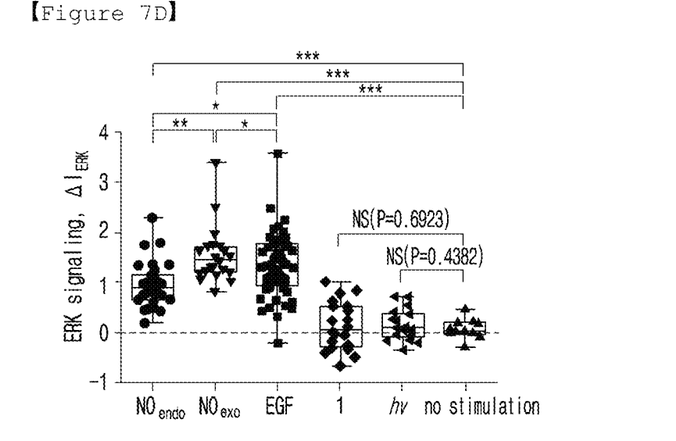
FIG. 7D is a diagram showing the ERK signal intensity changes at the single-cell level under each stimulation.
Figure 7E:
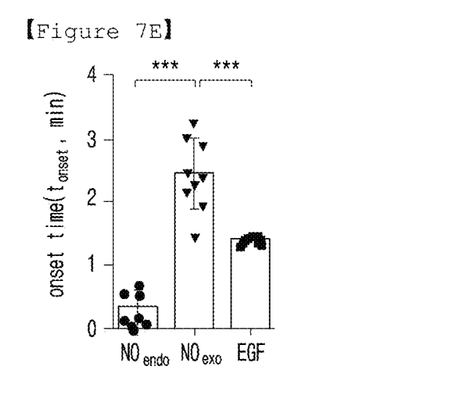
FIG. 7E is a diagram showing the onset time for ERK activation stimulated by EGF, endogenous or exogenous NO release.

To confirm the kinetic differences in endogenous/exogenous inputs, the onset time of ERK activation ($t_{onset}$) for individual cells was measured in Experimental Example 3-2 (FIG. 7C arrows and FIG. 7E). The $t_{onset}$ was measured by fitting $I_{ERK}$ (t) according to the plateau that followed the one-phase association method. As a result, it was confirmed the differences among the ERK activation conditions (endogenous: 0.6±0.5 min; exogenous: 4.8±1.1 min). These results were influenced by three potential factors: i) the duration of the diffusion of $NO_{Exo}$ through the culturing media, ii) the barrier to $NO_{Exo}$ penetration (through the lipid membrane), and iii) intrinsic differences in signaling pathway, depending on the controlled spatio-input. Considering the higher diffusion coefficients of NO in $H_2O$ and lipids ($D_{NO/H2O}$=2.2-4.5×10$^3$ μm$^2$ s$^{-1}$, $D_{NO/lipid}$=1.1-2.5×10$^3$ μm$^2$ s$^{-1}$) and given that its short lifetime (approximately 1 s) in the aqueous phase was shorter than the observed temporal scale of $t_{onset}$, the origin of the kinetic differences was neither due to diffusion (i) nor lipid barriers (ii), but was instead due to the different signaling pathway.

3-3. Evaluation Through EGFR Tracking

To confirm whether the activation of ERK by NO generated from the complex of Example 1 was induced by other receptors or membrane features, thus perturbing other signaling pathways, such as the MAPK pathway activated by the cauterization of EGF receptors (EGFRs) or by nonspecific disturbances caused by the formation of cellular membranes like lipid rafts, individual EGFRs in live cells were tracked, and analyzed.

Single-Particle Tracking and Diffusion Analysis.

Time-lapse dark-field microscope images were taken every 20 ms for 10 s. Lateral diffusion motion of protein was analyzed by particle trajectories. TrackMate plugin on Image J was used for single-particle tracking and trajectory analysis. For each particle, mean square displacement (MSD) was calculated from the x, y position and time information obtained from trajectory analysis; MSD(t)=<$(x_{i+n}-x_i)^2+(y_{i+n}-y_i)^2$>. The MSD versus time intervals were plotted up to the time lag (t) equivalent to $\frac{1}{10}^{th}$ of the trajectory duration, then fitted to a linear equation corresponding to the Brownian motion. Diffusion coefficient (D) was calculated from the slope of the first ten points of the MSD plot; MSD=4Dt.

Figure 8A:
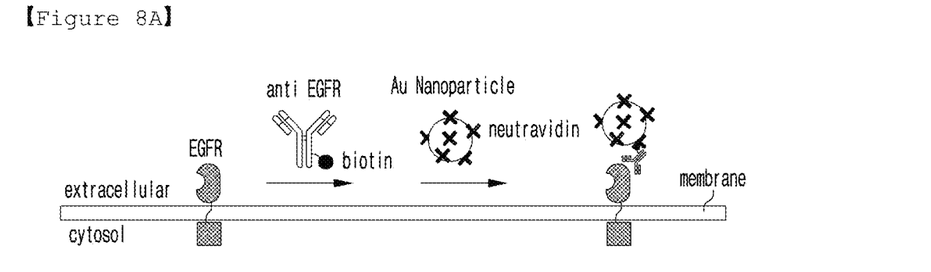
FIG. 8A is a diagram illustrating how an EGFR is targeted using a biotinylated EGFR antibody and neutravidin-conjugated gold nanoparticles.
Figure 8B:
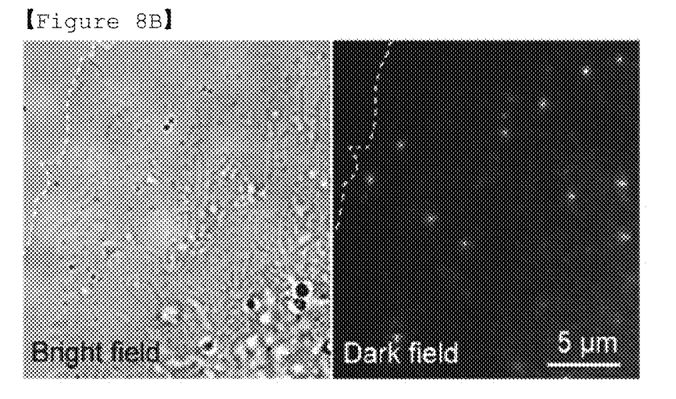
FIG. 8B is a diagram showing the bright-(left) and dark-(right) field images of the probes selectively bound to the receptor without non-specific binding.

For single-molecule tracking of EGFR, anti-EGFR (EGFR anti-bodies) was conjugated to gold nanoparticles (AuNPs, 50 nm in diameter) using the biotin-neutravidin interaction (FIG. 8A), achieving high specificity (FIG. 8B).

FIG. 8A shows how the EGFR was targeted using biotinylated anti-EGFR and neutravidin-conjugated 50 nm AuNPs.

The EGFRs that were labeled with anti-EGFR-AuNPs were visualized using dark-field microscopy at the single-molecule level. It was confirmed through the bright-(left) and dark-(right) field images shown in FIG. 8B that the probe was selectively attached to the receptor without specific binding.

Figure 8C:
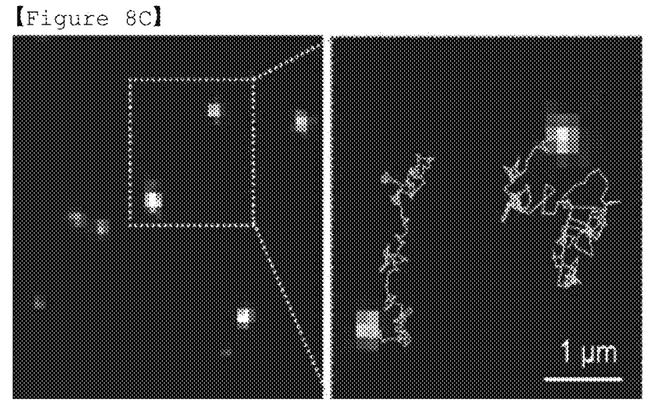
FIG. 8C is a diagram showing the dark-field images of particle movements (left) and their corresponding trajectories (right).
Figure 8D:
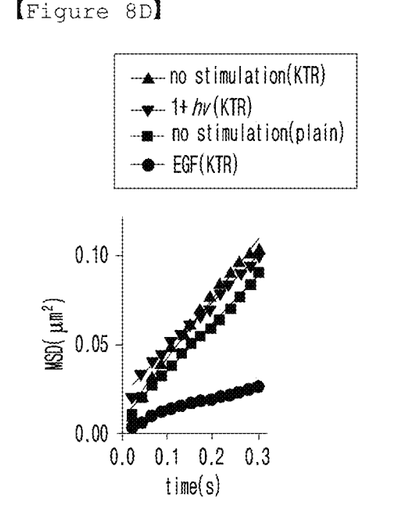
FIG. 8D is a diagram illustrating the mean square displacement (MSD) according to the time lag of particles.
Figure 8E:
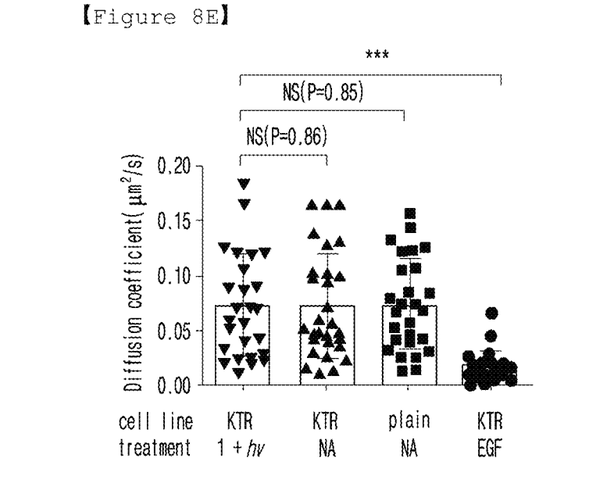
FIG. 8E is a diagram illustrating the diffusion coefficients analyzed via single particle tracking.

The two-dimensional trajectories of the individual AuNPs were shown in FIG. 8C. The calculated mean square displacement (MSD) from these trajectories exhibited three interesting phenomena: i) the receptors followed 2D Brownian diffusion, based on the linear fitting of the MSD, ii) nearly identical diffusion coefficients of EGFR ($D_{EGFR}$) were measured in the control, ERK-KTR cells (0.071 $\mu m^2$ $s^{-1}$), $NO_{Exo}$-treated ERK-KTR cells (0.072 $\mu m^2$ $s^{-1}$), and plain U2OS cells (0.073 $\mu m^2$ $s^{-1}$), indicating that neither the engineering of cell nor $NO_{Exo}$ treatment affected the mobility of EGFRs, and iii) the $D_{EGFR}$ under the EGF-treated conditions was 0.017 $\mu m^2$ $s^{-1}$ ($P<0.001$); this result was consistent with previous research, wherein the $D_{EGFR}$ was shown to be slowed after activation induced by EGF binding. These results indicate that the NO-generating conditions do not affect EGFR association, or its intrinsic functions. Consequently, the NO molecules released from the complex of Example 1 did not induce ERK signaling by non-specifically perturbing membrane proteins, including EGFR or membrane organization, thus each has its own pathway for the activation of ERK signaling.

The present inventors have identified the NO molecule delivery system and confirmed its artificial regulatory effects on endogenous/exogenous cellular signaling in detail. The $Co^{III}$-nitrosyl complex according to the present invention is a NO carrier and exhibits photocleavable properties following the first-order kinetics. Since the cobalt complex according to the present invention is biocompatible, it does not interfere with the membrane receptors, and their membrane permeability and downstream signaling can be activated without any perturbations.

As mentioned above, the present invention has been described in detail through the preferred preparative examples, examples and experimental examples, but the scope of the present invention is not limited to the specific examples, and should be interpreted by the appended claims. In addition, those of ordinary skill in the art should understand that many modifications and variations are possible without departing from the scope of the present invention.

What is claimed is:

1. A cobalt-nitrosyl complex represented by formula 1 below:

$$[Co^{III}(L)(NO)(sol)]^{2+} \quad \text{[Formula 1]}$$

(In formula 1, sol is a compound selected from the group consisting of H$_2$O, CH$_3$CN, tetrahydrofuran, dioxane, dichloromethane, ether solvents such as 1,2-dimethoxyethane, aromatic hydrocarbon solvents such as benzene, toluene and xylene, dimethyl formamide (DMF), and dimethyl sulfoxide (DMSO);

L is

R$^1$ and R$^2$ are independently hydrogen, nonsubstituted or substituted straight or branched C$_{1-10}$ alkyl, C$_{3-10}$ cycloalkyl, C$_{6-10}$ aryl, or C$_{6-10}$ aryl C$_{1-3}$ alkyl, wherein the substituted straight or branched C$_{1-10}$ alkyl, C$_{3-10}$ cycloalkyl, C$_{6-10}$ aryl, or C$_{6-10}$ aryl C$_{1-3}$ alkyl is independently C$_{1-10}$ alkyl, C$_{3-10}$ cycloalkyl, C$_{6-10}$ aryl, or C$_{6-10}$ aryl C$_{1-3}$ alkyl substituted with one or more substituents selected from the group consisting of halogen, hydroxy, nitro, nitryl, C$_{1-3}$ alkyl and C$_{1-3}$ alkoxy;

X and Y are independently hydrogen, halogen, nonsubstituted or substituted straight or branched C$_{1-8}$ alkyl, C$_{3-8}$ cycloalkyl, C$_{6-8}$ aryl, or C$_{6-8}$ aryl C$_{1-3}$ alkyl, wherein the substituted straight or branched C$_{1-8}$ alkyl, C$_{3-8}$ cycloalkyl, C$_{6-8}$ aryl, or C$_{6-8}$ aryl C$_{1-3}$ alkyl is independently C$_{1-8}$ alkyl, C$_{3-8}$ cycloalkyl, C$_{6-8}$ aryl, or C$_{6-8}$ aryl C$_{1-3}$ alkyl substituted with one or more substituents selected from the group consisting of halogen, hydroxy, nitro, nitryl, C$_{1-3}$ alkyl and C$_{1-3}$ alkoxy; and m and n are independently integers of 0 to 3).

2. The cobalt-nitrosyl complex according to claim 1, wherein:

R$^1$ and R$^2$ are independently nonsubstituted or substituted straight or branched C$_{1-8}$ alkyl, or C$_{3-6}$ cycloalkyl, wherein the substituted straight or branched C$_{1-8}$ alkyl, or C$_{3-6}$ cycloalkyl is independently C$_{1-8}$ alkyl, or C$_{3-6}$ cycloalkyl substituted with one or more substituents selected from the group consisting of halogen, hydroxy, nitro, nitryl, C$_{1-3}$ alkyl and C$_{1-3}$ alkoxy;

X and Y are independently hydrogen, halogen, nonsubstituted or substituted straight or branched C$_{1-5}$ alkyl, or C$_{3-6}$ cycloalkyl, wherein the substituted straight or branched C$_{1-5}$ alkyl, or C$_{3-6}$ cycloalkyl, is independently C$_{1-5}$ alkyl, or C$_{3-6}$ cycloalkyl substituted with one or more substituents selected from the group consisting of halogen, hydroxy, nitro, nitryl, C$_{1-3}$ alkyl and C$_{1-3}$ alkoxy; and m and n are independently integers of 0 to 2.

3. The cobalt-nitrosyl complex according to claim 1, wherein:

R$^1$ and R$^2$ are independently nonsubstituted or substituted straight or branched C$_{1-3}$ alkyl, wherein the substituted straight or branched C$_{1-3}$ alkyl is C$_{1-3}$ alkyl substituted with one or more substituents selected from the group consisting of halogen, hydroxy, C$_{1-3}$ alkyl and C$_{1-3}$ alkoxy;

X and Y are independently hydrogen, nonsubstituted or substituted straight or branched C$_{1-2}$ alkyl, wherein the substituted straight or branched C$_{1-2}$ alkyl is independently C$_{1-2}$ alkyl substituted with one or more substituents selected from the group consisting of halogen, hydroxy, C$_{1-3}$ alkyl and C$_{1-3}$ alkoxy; and m and n are independently integers of 0 or 1.

4. The cobalt-nitrosyl complex according to claim 1, wherein:

sol is CH$_3$CN; and

L is N,N'-dimethyl-2,11-diaza[3,3] (2,6)-pyridinophane.

5. A preparation method of a cobalt-nitrosyl complex represented by formula 1 of claim 1 comprising the step of preparing a compound represented by formula 1 by reacting a compound represented by formula 2 with nitric oxide (NO), as shown in reaction formula 1 below:

[Reaction Formula 1]

(In reaction formula 1,
L and sol are as defined in formula 1 of claim 1).

6. A nitric oxide carrier comprising the cobalt-nitrosyl complex represented by formula 1 of claim 1.

7. The nitric oxide carrier according to claim 6, wherein nitric oxide is released when the complex is irradiated with light.

8. The nitric oxide carrier according to claim 6, wherein the nitric oxide carrier artificially regulates cell signaling.

* * * * *

SEQUENCE LISTING

```
<160> NUMBER OF SEQ ID NOS: 4

<210> SEQ ID NO 1
<211> LENGTH: 45
<212> TYPE: PRT
<213> ORGANISM: Artificial Sequence
<220> FEATURE:
<223> OTHER INFORMATION: synthetic sequence

<400> SEQUENCE: 1

Met Lys Gly Arg Lys Pro Arg Asp Leu Glu Leu Pro Leu Ser Pro Ser
1               5                   10                  15

Leu Leu Gly Gly Gln Gly Pro Glu Arg Thr Pro Gly Ser Gly Thr Ser
            20                  25                  30

Ser Gly Leu Gln Ala Pro Gly Pro Ala Leu Ser Pro Ser
        35                  40                  45

<210> SEQ ID NO 2
<211> LENGTH: 37
<212> TYPE: PRT
<213> ORGANISM: Artificial Sequence
<220> FEATURE:
<223> OTHER INFORMATION: synthetic sequence

<400> SEQUENCE: 2

Lys Arg Ser Gly Leu Glu Asp Pro Ala Thr Pro Ser Lys Lys Pro Arg
1               5                   10                  15

Thr Pro Ser Val Ser Ser Arg Leu Glu Arg Leu Thr Leu Gln Ser Ser
            20                  25                  30

Phe Gln Phe Pro Ser
        35

<210> SEQ ID NO 3
<211> LENGTH: 135
<212> TYPE: DNA
<213> ORGANISM: Artificial Sequence
<220> FEATURE:
<223> OTHER INFORMATION: synthetic sequence
```

```
<400> SEQUENCE: 3
atgaagggca ggaagcccag ggacctggag ctgcccctga gccccagcct gctgggcggc    60
cagggccccg agaggacccc cggcagcggc accagcagcg gcctgcaggc ccccggcccc   120
gccctgagcc ccagc                                                    135

<210> SEQ ID NO 4
<211> LENGTH: 111
<212> TYPE: DNA
<213> ORGANISM: Artificial Sequence
<220> FEATURE:
<223> OTHER INFORMATION: synthetic sequence

<400> SEQUENCE: 4
aagaggagcg gcctggagga ccccgccacc cccagcaaga agcccaggac ccccagcgtg    60
agcagcaggc tggagaggct gaccctgcag agcagcttcc agttcccag c              111
```